United States Patent
Maldari

(10) Patent No.: US 11,666,764 B2
(45) Date of Patent: Jun. 6, 2023

(54) SYSTEM FOR MEASUREMENT OF IMPEDANCE CARDIOGRAPHY

(71) Applicant: SORIN CRM SAS, Clamart (FR)

(72) Inventor: Mirko Maldari, Paris (FR)

(73) Assignee: Sorin CRM SAS, Clamart (FR)

( * ) Notice: Subject to any disclaimer, the term of this patent is extended or adjusted under 35 U.S.C. 154(b) by 76 days.

(21) Appl. No.: 17/109,864

(22) Filed: Dec. 2, 2020

(65) Prior Publication Data
US 2021/0162218 A1 Jun. 3, 2021

(30) Foreign Application Priority Data
Dec. 3, 2019 (FR) ...................................... 1913676

(51) Int. Cl.
| | | |
|---|---|---|
| *A61N 1/37* | (2006.01) | |
| *A61N 1/39* | (2006.01) | |
| *A61N 1/365* | (2006.01) | |
| *A61N 1/372* | (2006.01) | |

(52) U.S. Cl.
CPC ......... *A61N 1/371* (2013.01); *A61N 1/36521* (2013.01); *A61N 1/37235* (2013.01); *A61N 1/39622* (2017.08)

(58) Field of Classification Search
None
See application file for complete search history.

(56) References Cited

U.S. PATENT DOCUMENTS

| | | | | |
|---|---|---|---|---|
| 4,291,699 A | * | 9/1981 | Geddes | A61B 5/0535 607/6 |
| 4,987,897 A | | 1/1991 | Funke | |
| 9,308,377 B1 | * | 4/2016 | Schaefer | A61N 1/3787 |
| 2012/0035490 A1 | | 2/2012 | Shen et al. | |
| 2012/0197350 A1 | * | 8/2012 | Roberts | A61B 5/0028 607/60 |
| 2018/0206724 A1 | * | 7/2018 | Chin | A61N 1/37276 |
| 2018/0289279 A1 | * | 10/2018 | Ren | A61B 5/369 |

(Continued)

FOREIGN PATENT DOCUMENTS

WO WO-00/78391 A1 12/2000

OTHER PUBLICATIONS

France Search Report on French Patent Application No. 1913676 dated Aug. 12, 2020.

(Continued)

*Primary Examiner* — Catherine M Voorhees
*Assistant Examiner* — Elizabeth K So
(74) *Attorney, Agent, or Firm* — Foley & Lardner LLP

(57) ABSTRACT

The present invention relates to a system of multiple implantable medical devices for an impedance measurement comprising a first implantable medical device, at least a second implantable medical device distinct from the first implantable medical device and; an analysis module comprising at least one amplifier and one envelope detector, one of the first implantable medical device or the second implantable medical device being a subcutaneous implantable cardioverter defibrillator or a subcutaneous loop recorder, and the other of the first implantable medical device or the second implantable medical device being an implantable endocardial device.

14 Claims, 5 Drawing Sheets

(56) References Cited

U.S. PATENT DOCUMENTS

2019/0111268 A1 4/2019 Christie et al.

OTHER PUBLICATIONS

Neal Bhatia et al: "Leadless pacemakers: a contemporary review", Journal of geriatric cardiology : JGC, Apr. 1, 2018 (Apr. 1, 2018), pp. 249-253, XP055698069, China DOI: 10.11909/j.issn.1671-5411. 2018.04.002 Extrait de !'Internet: URL:https://www.ncbi.nlm.nih. gov/pmc/articles/PMC5997619/pdf/jgc-15-04-249.pdf.
"Leadless pacemakers: a contemporary review" by Neal Bhatia and Mikheal El-Chami, from Journal of geriatric Cardiology, 2018 (5 pages).
Foreign Search Report on EP Appl. Ser. No. 20211524.2 dated Mar. 30, 2021 (8 pages).

\* cited by examiner

SYSTEM FOR MEASUREMENT OF IMPEDANCE CARDIOGRAPHY

CROSS-REFERENCE TO RELATED PATENT APPLICATIONS

This application claims the benefit of and priority to French Patent Application No. 1913676, filed Dec. 3, 2019, which is incorporated by reference herein in its entirety.

BACKGROUND

The present invention relates to a system configured for carrying out a measurement of impedance cardiography.

The measurement of impedance cardiography can be used for determining physiologic information related to a patient, such as the heart activity as described in the document WO 0078391 A1.

The document WO 0078391 A1 relates to a cardiac rhythm management apparatus configured for performing impedance plethysmography by means of plural endocardial leads provided with electrodes. The apparatus according to the document WO 0078391 A1 performs a real-time impedance measurement in the right ventricle from which hemodynamic information related to the cardiac performance— such as the measurement of the left ventricular stroke volume, the determination of the ejection fraction or the rate of filling—can be determined.

Nonetheless, the apparatus described in the document WO 0078391 A1 is not suitable for retrieving respiration information from the impedance measurement, much less for discriminating respiration information from hemodynamic information. Thus, the apparatus described in the document WO 0078391 A1 is also unable to differentiate a respiratory artifact in the impedance measurement.

It is, however, necessary to be able to retrieve and discriminate respiration and hemodynamic information relating to pulmonary activity and blood flow for the diagnosis and the monitoring of cardiac insufficiency (also known as heart failure). Cardiac insufficiency is an inability of the heart to pump enough blood to ensure satisfactory blood flow throughout the whole body. Cardiac insufficiency has a chronic and progressive evolution, generally slow, which may take place over a number of years.

The document US 2019/0111268 A relates to the determination of the impedance into an extra-cardiovascular location of a patient by means of an implantable cardioverter-defibrillator with a subcutaneous lead. The document US 2019/0111268 A describes that a same pair of electrodes on the subcutaneous lead acts as both dipole transmitter and dipole receiver to respectively transmit and receive an impedance signal representative of the local impedance in the vicinity of the pair of electrodes.

It appears that the detection of cardiac events as described in the document US 2019/0111268 A to identify a heart rhythm disorder is also not suitable for monitoring cardiac insufficiency. Indeed, the impedance measurement proposed in the document US 2019/0111268 A is relative to a local measurement, which makes it less sensitive to lung function and to the circulation of blood in the neighboring organs. However, respiratory and hemodynamic information relating to lung function and to the circulation of blood in the neighboring organs is also information which is useful to diagnosis and to monitoring cardiac insufficiency.

The object of the present invention is to propose a system allowing to improve and optimize the diagnosis and the monitoring of cardiac insufficiency (also known as heart failure), in particular from the collection (capture) of respiratory and hemodynamic information via an impedance measurement.

The object of the present invention is achieved with a system of multiple implantable medical devices for an impedance measurement comprising: a first implantable medical device comprising at least one dipole emitter formed by two electrodes connected to a generator and configured for emitting an electrical signal, at least a second implantable medical device distinct from the first implantable medical device and comprising at least one dipole receiver formed by two electrodes, the dipole receiver being configured to capture the electrical signal emitted by means of the dipole emitter of the first implantable medical device; an analysis module comprising at least one amplifier and one envelope detector, one of the first implantable medical device or the second implantable medical device being a subcutaneous implantable cardioverter defibrillator or a subcutaneous loop recorder, and the other of the first implantable medical device or the second implantable medical device being an implantable endocardial device.

The fact that the system has at least four electrodes, such that the dipole emitter is distinct from the dipole receiver, and that one of the dipoles is comprised in a subcutaneous device while the other dipole is comprised in an endocardial device, makes it possible to obtain an impedance measurement more global and thus more representative of the surrounding medium, in particular more global and more representative of the surrounding medium than a measurement between only two electrodes of the same lead. Indeed, the present system allows retrieving physiologic mechanical information by means of two distinct devices by analyzing the captured electrical signal, the amplitude of which being modulated according to the electrical properties of the propagation media between the dipole emitter and the dipole receiver. Hence, by means of the analysis module, in particular of the envelope detector which is able to perform amplitude demodulation of the captured signal, it is possible to retrieve information which can be correlated to physiological parameters such as the cardiac output, the preejection period, the left ventricular ejection fraction, the heart rate, the respiration rate, etc., which are particularly useful for the diagnosis and monitoring of cardiac insufficiency.

SUMMARY

The present invention may be further improved by the following embodiments.

According to one embodiment, the analysis module can further comprise an analog-digital converter and at least one digital filtering means configured to treat the captured electrical signal.

Thus, following the envelope detector, the captured and detected signal can be sampled by the analog-digital converter of the analysis module and digitally filtered to discriminate respiration information from hemodynamic information.

According to one embodiment, the analysis module can comprise a low pass digital filter configured to retrieve physiologic information of the captured electrical signal, in particular a low pass digital filter with a cutoff frequency comprised between 0.5 Hz and 5 Hz, more in particular with a cutoff frequency of 1 Hz.

Thus, the cutoff frequency of the digital filter can be adjusted according to the characteristics of each particular physiological parameter to be observed, in this case respiration parameters.

According to one embodiment, the analysis module can comprise a bandpass digital filter configured to retrieve hemodynamic information of the captured electrical signal, in particular a bandpass digital filter with a bandwidth comprised between 0.5 Hz and 30 Hz.

The frequency range of 0.5 Hz to 30 Hz allows both filtering of the respiratory artifact by cutting frequencies below 0.5 Hz and filtering of high-frequency noises, i.e. noises with a frequency above 30 Hz. Thus, the system can be used to recover hemodynamic and respiratory information from the same signal acquisition using appropriate digital filters to discriminate between the different information.

According to one embodiment, the analysis module can comprise a bandpass low noise amplifier configured to amplify the signal captured by the dipole receiver.

Thus, the analysis module is configured to pass and amplify only a predefined useful frequency of the captured signal.

According to one embodiment, the analysis module can comprise a plurality of low noise amplifiers selectable according to the position of each dipole emitter with respect to each dipole receiver.

Thus, depending on the attenuation due to the mutual position of the dipoles, the analysis module of the system can select the appropriate amplifier. The analysis module of the present system is thus able to adapt to the anatomy of each patient, which is different for each patient. In addition, in this case, the energy consumption of the system can be optimized.

According to one embodiment, the implantable endocardial device can be a leadless cardiac pacemaker.

Thus, using the subcutaneous implantable device as an emitter, and the leadless cardiac pacemaker as a receiver and implanted in the right ventricle, the atrial kick information can be retrieved by the leadless cardiac pacemaker because the mechanical activity of the atrium changes both the amount of blood in the right ventricle and the orientation of the leadless cardiac pacemaker. The atrial contraction information can be used by the leadless cardiac pacemaker to adapt the stimulation to the normal atrial activity.

According to one embodiment, the system can further comprise at least a second leadless cardiac pacemaker provided with at least one dipole receiver and/or dipole emitter, and the system being configured to adapt an electrical pulse delivered by means of one the implantable devices of the system based on the electrical signal captured by at least one dipole receiver of the system.

Thus, when the first leadless cardiac pacemaker is implanted in the left ventricle and the second leadless cardiac pacemaker is implanted in the right ventricle, the system constitutes a Cardiac Resynchronization Therapy (CRT) system adapted for the treatment of cardiac insufficiency, in addition of being configured for the diagnosis and monitoring of cardiac insufficiency.

By means of such a system, the therapy delivered by applying electric pulses to treat cardiac insufficiency can be adapted and optimized by taking into account the physiological parameters extracted from the electrical signals captured by the system. In particular, such a system is able to synchronize the interventricular contraction by means of leadless cardiac pacemakers implanted in each ventricle.

According to one embodiment, the dipole emitter can emit an electrical signal having a variable amplitude.

Thus, the amplitude of the electrical signal emitted by the dipole emitter can be adjusted once the implantable devices, and thus the dipoles emitter/receiver, are implanted in a patient's body in order to obtain a suitable signal-to-noise ratio for detection at the dipole receiver.

According to one embodiment, the first implantable medical device can comprise a telemetry module configured to communicate with an external device such that the amplitude of the electrical signal emitted by the dipole emitter is adjustable by telemetry.

Thus, the adjustment of the amplitude of the emitted electrical signal can be further optimized.

BRIEF DESCRIPTION OF THE DRAWINGS

The invention and its advantages will be explained in more detail in the following by means of preferred embodiment and by means of the following accompanying figures, in which.

DETAILED DESCRIPTION

The invention will now be described in more detail using advantageous embodiments by way of example and with reference to the figures. The embodiments described are simply configurations which are possible and it should be borne in mind that the individual features as described above may be provided independently of each other or may be omitted altogether when carrying out the present invention.

Figure 1:
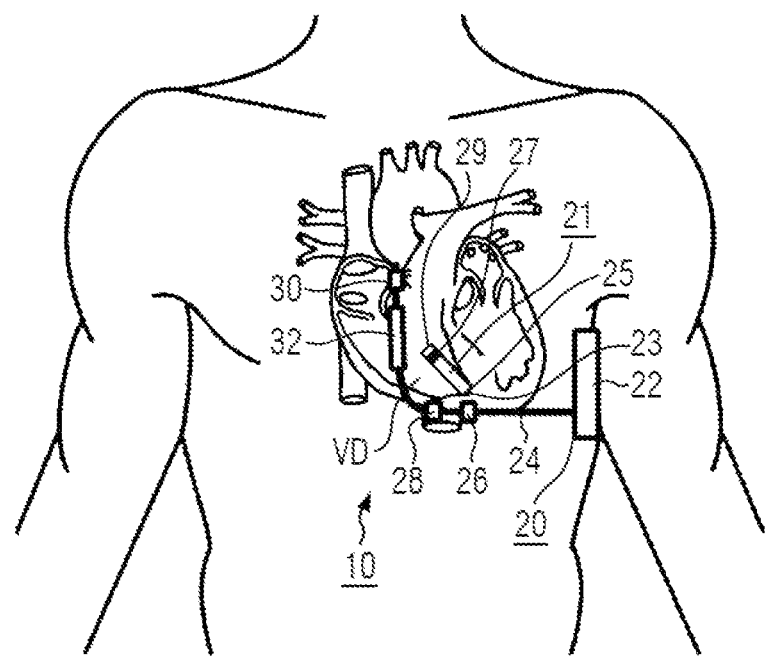
FIG. 1 shows a system according to the present invention comprising two devices.

FIG. 1 represents a system 10 according to the present invention comprising two implantable devices. In particular, the system 10 of multi-devices shown in FIG. 1 comprises an implantable subcutaneous device 20 and an endocardial device 21 which is, in the example of FIG. 1, a leadless cardiac pacemaker 21. In the following, the implantable subcutaneous device 20 will be described with even reference numerals while the endocardial device 21 will be described with odd reference numerals.

The implantable subcutaneous device 20 as shown in FIG. 1 comprises a housing 22 and a subcutaneous lead 24 provided with three electrodes 26, 28, 30 and a defibrillation electrode 32. The implantable subcutaneous device 20 is thus suitable for comprising at least one dipole emitter and one dipole receiver wherein the electrodes of each dipole are distinct from each other.

Table 1 below lists all configurations of the dipole emitters and dipole receivers which may be used in the implantable subcutaneous device 20.

TABLE 1

| # | Emitter or receiver dipole |
|---|---|
| 1 | 22-26 |
| 2 | 22-28 |
| 3 | 22-30 |
| 4 | 22-32 |
| 5 | 26-28 |
| 6 | 26-30 |
| 7 | 26-32 |
| 8 | 28-30 |
| 9 | 28-32 |
| 10 | 30-32 |

As indicated in Table 1, one of the electrodes may be constituted by the housing 22 of the implantable subcutaneous device 20. Any of the combinations of electrodes may be used, including the defibrillation electrode 32.

In a variation, an event recorder or an implantable loop recorder comprising at least a pair of electrodes could be used instead of the implantable subcutaneous device 20.

The leadless capsule pacemaker 21 comprises a tip electrode 23 disposed at one distal end 25 of the capsule 21, and a ring electrode 27 disposed towards a proximal end 29 of the capsule. The electrodes 23, 27 may form a dipole receiver or a dipole emitter. It should be noted that the present invention does not limit itself to the use of a tip electrode and a ring electrode but the present invention can be implemented by means of any types of electrodes comprised in a leadless cardiac pacemaker.

In a variation, a cardiac device with an endocardial lead comprising at least one pair of electrodes may be used instead of the leadless cardiac pacemaker 21.

Each of the implantable subcutaneous device 20 and the leadless cardiac pacemaker 21 comprises electrodes 22, 26, 28, 30, 32; 23, 27 which may act as dipole receiver and dipole emitter. Hence, both the implantable subcutaneous device 20 and the leadless cardiac pacemaker 21 may act as emitter or receiver in the implantable system 10 according to the present invention. Moreover, a practitioner may advantageously select the configuration of the dipole emitter and the dipole receiver which is the most suitable for the physiological parameters that are to be captured. The different possible configurations of dipole emitter/dipole receiver with the system 10 are listed in the Table 2 here below.

TABLE 2

| # | Emitter dipole | Receiver dipole |
|---|---|---|
| 1 | 22-26 | 23-27 |
| 2 | 22-28 | 23-27 |
| 3 | 22-30 | 23-27 |
| 4 | 22-32 | 23-27 |
| 5 | 26-28 | 23-27 |
| 6 | 26-30 | 23-27 |
| 7 | 26-32 | 23-27 |
| 8 | 28-30 | 23-27 |
| 9 | 28-32 | 23-27 |
| 10 | 30-32 | 23-27 |
| 11 | 23-27 | 22-26 |
| 12 | 23-27 | 22-28 |

TABLE 2-continued

| # | Emitter dipole | Receiver dipole |
|---|---|---|
| 13 | 23-27 | 22-30 |
| 14 | 23-27 | 22-32 |
| 15 | 23-27 | 26-28 |
| 16 | 23-27 | 26-30 |
| 17 | 23-27 | 26-32 |
| 18 | 23-27 | 28-30 |
| 19 | 23-27 | 28-32 |
| 20 | 23-27 | 30-32 |

Thus, it is possible to select the configuration of the dipoles which is the most sensitive and/or the most energy-saving, in particular during the lifetime of a patient in whom the devices 20, 21 are implanted. This selection may be carried out in real time using a telemetry module.

The implantation, as shown in FIG. 1, of the implantable subcutaneous device 20 and the leadless cardiac pacemaker 21, which is implanted in the right ventricle VD, is suitable for a trans-thoracic measurement and allows detecting changes in the volume of a chamber of the heart other than the chamber in which the leadless cardiac pacemaker 21 is implanted.

As an example, by using the implantable subcutaneous device 20 as emitter, in particular the pair of electrodes 26, 30, and the leadless cardiac pacemaker 21 implanted in the right ventricle VD as receiver (i.e. the pair of electrodes 23, 27), the information relative to the contraction of the atrium ("atrial kick") may be recovered by the leadless cardiac pacemaker 21, given that the mechanical activity of the atrium modifies both the quantity of blood present in the right ventricle VD and the orientation of the leadless cardiac pacemaker 21. The information relative to the contraction of the atrium may be used by the leadless cardiac pacemaker 21 in order to adapt the stimulation to the normal activity of the atrium.

In addition, because the system 10 has at least four electrodes such that the dipole emitter is distinct from the dipole receiver, it is possible to obtain a measurement of the impedance which is more global and thus more representative of the surrounding medium than a measurement between only two electrodes of the same lead.

Figure 2:
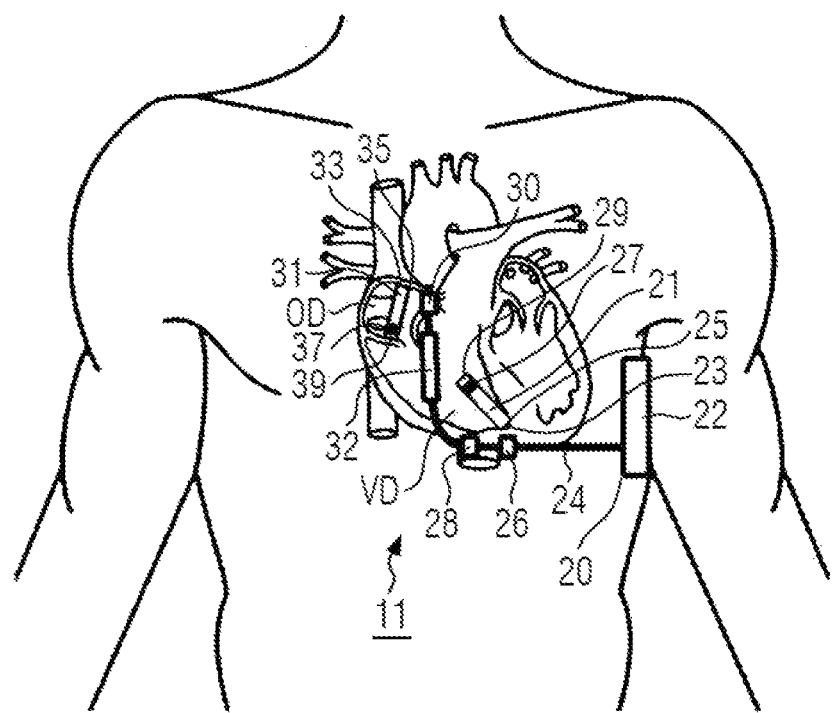
FIG. 2 shows a system according to the present invention comprising three devices.

FIG. 2 represents a system 11 according to the present invention comprising three implantable devices 20, 21 and 31.

The elements with the same reference numerals already used for the description of FIG. 1 will not be described again in detail; reference should be made to their descriptions above.

The system 11 comprises one additional implantable device 31 in comparison to the system 10 shown in FIG. 1.

The additional implantable device 31 of system 11 shown in FIG. 2 is a leadless cardiac pacemaker 31, implanted in the right atrium. In a variation, the leadless cardiac pacemaker 31 is provided for implantation in the left ventricle VG. Depending on the chamber in which the leadless cardiac pacemaker 31 is implanted, either the right atrium OD or the left ventricle VG can be stimulated.

As for the first the leadless cardiac pacemaker 21, the second leadless cardiac pacemaker 31 comprises a tip electrode 33 disposed at one distal end 35 of the capsule 31, and a ring electrode 37 disposed towards a proximal end 39 of the capsule 31.

The electrodes 23, 27 may form a dipole receiver or a dipole emitter.

It should be noted that the present invention does not limit itself to the use of a tip electrode and a ring electrode but the present invention can be implemented by means of any types of electrodes comprised in a leadless cardiac pacemaker.

The different configurations of dipole emitter/dipole possible by means of the system 11 comprising three devices 20, 21, 31 are listed in the Table 3 here below.

The possible configurations between only two of the three devices 20, 21, 31 are also listed in the Table 3.

TABLE 3

| # | Device 20 | Capsule 21 | Capsule 31 |
|---|---|---|---|
| 1 | Emitter dipole | Receiver dipole | Receiver dipole |
| 2 | Receiver dipole | Emitter dipole | Receiver dipole |
| 3 | Receiver dipole | Receiver dipole | Emitter dipole |
| 4 | Emitter dipole | Receiver dipole | — |
| 5 | Emitter dipole | — | Receiver dipole |
| 6 | — | Emitter dipole | Receiver dipole |
| 7 | Receiver dipole | Emitter dipole | — |
| 8 | Receiver dipole | — | Emitter dipole |
| 9 | — | Receiver dipole | Emitter dipole |

Hence, the system 11 is even more suitable for a trans-thoracic measurement and can be used to detect the changes in volume observed in the right ventricle VD and in the right atrium OD. Indeed, the electrical signal captured by means of the capsule 21 (implanted in the right ventricle VD) and the electrical signal captured by means of the capsule 31 (implanted in the right atrium in the embodiment represented by FIG. 2) may be different from each other.

As mentioned above, the capsule 21 may, in a variation, be implanted in the left ventricle VG.

In any case, one of the electrical signals may provide more useful information than the other captured electrical signal. The system 11 can thus determine the most suitable propagation channel for the determination of the desired respiratory and hemodynamic parameters.

The system 11 can thus be used to provide a more exhaustive view of the trans-thoracic measurement. Moreover, the system 11 is suitable for stimulating the heart in the right atrium OD.

Figure 3:
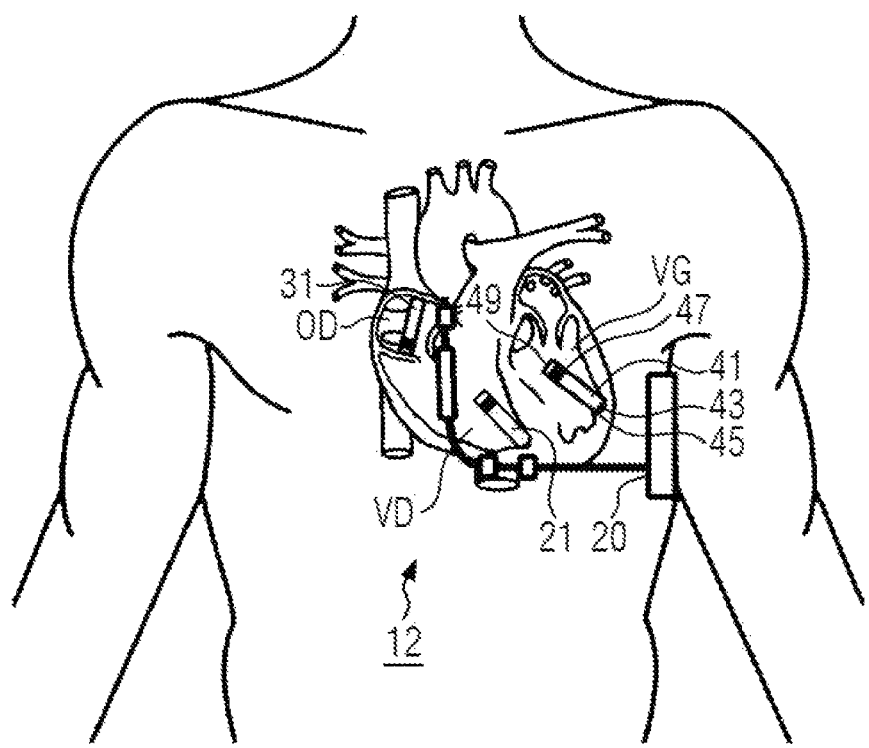
FIG. 3 shows a system according to the present invention comprising four devices.

FIG. 3 represents a system 12 according to the present invention comprising four implantable devices 20, 21, 31 and 41.

The elements with the same reference numerals already used for the description of FIGS. 1 and 2 will not be described again in detail; reference should be made to their descriptions above.

The system 12 comprises one additional implantable device 41 in comparison to the system 11 shown in FIG. 2.

The additional implantable device of system 12, shown in FIG. 3 is a leadless cardiac pacemaker 41 implanted in the left ventricle VG.

As for the first the leadless cardiac pacemaker 21 and the second leadless cardiac pacemaker 31, the third leadless cardiac pacemaker 41 comprises a tip electrode 43 disposed at one distal end 45 of the capsule 41, and a ring electrode 47 disposed towards a proximal end 49 of the capsule 41. The electrodes 43, 47 may form a dipole receiver or a dipole emitter.

It should be noted that the present invention does not limit itself to the use of a tip electrode and a ring electrode but the present invention can be implemented by means of any types of electrodes comprised in a leadless cardiac pacemaker.

The first leadless cardiac pacemaker 21 implanted in the right ventricle VD, the second leadless cardiac pacemaker 31 implanted in the right atrium OD, and the third leadless cardiac pacemaker 41 implanted in the left ventricle VG form constitute a leadless implantable cardiac resynchronization system 50, i.e. without lead.

The implantable cardiac resynchronization system 50 known as a "triple chamber" system (right ventricle VD, right atrium OD and left ventricle VG) is suitable for the treatment of cardiac insufficiency (also known as heart failure), in addition of being configured for the diagnosis and the monitoring of cardiac insufficiency. In fact, in the implantable cardiac resynchronization system 50, the therapy can be optimized by taking into account physiological parameters recovered from the electrical signals. The implantable cardiac resynchronization system 50 is particularly suitable for synchronizing the intraventricular contraction and the interventricular contraction by means of the third leadless pacemaker pacemaker 41 implanted in the left ventricle VG.

Both the implantable subcutaneous device 20 and the leadless cardiac pacemakers 21, 31, 41 may act as emitter or receiver in the implantable system 12 according to the present invention. Moreover, a practitioner may advantageously select the configuration of the dipole emitter and the dipole receiver which is the most suitable for the physiological parameters that are to be captured.

Figure 4:
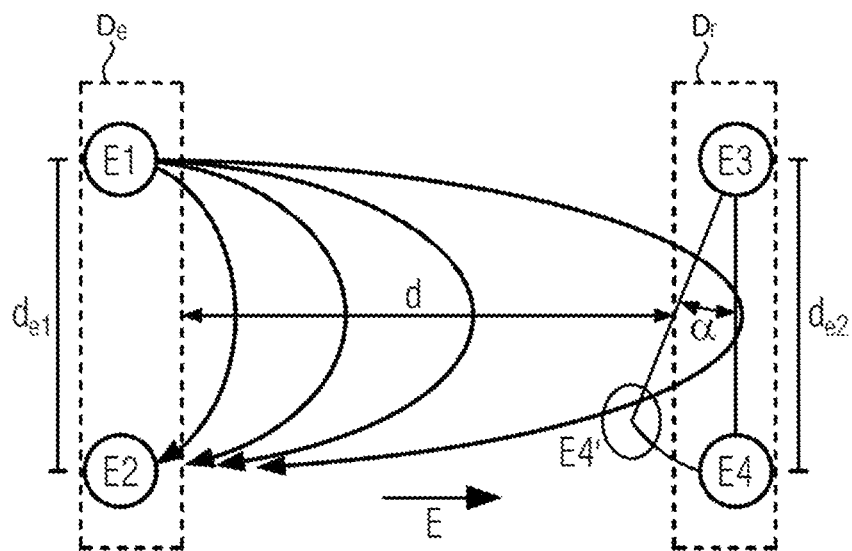
FIG. 4 shows a schematic view of the propagation of an electrical signal between a dipole emitter and a dipole receiver of the system according to the present invention.

FIG. 4 shows schematically the propagation of an electrical signal from a dipole emitter to a dipole receiver of an implantable medical system according to the present invention, as the system 10 shown in FIG. 1, the system 11 shown in FIG. 2 or the system 12 shown in FIG. 3.

The FIG. 4 shows a dipole emitter $D_e$ formed by an electrode E1 and an electrode E2. The dipole emitter $D_e$ is comprised in a subcutaneous or endocardial implantable device, as one of the devices 20, 21, 31 or 41 shown in FIGS. 1 à 3.

By applying an electrical signal, the dipole emitter $D_e$ is used to generate an electric field E which propagates through the tissues of a human body to a dipole receiver $D_r$. The dipole receiver $D_r$ is formed by an E3 electrode and an E4 electrode. The dipole receiver $D_r$ detects a potential difference of the electric field E by means of the detected electric signal.

The detected electrical signal principally depends on four factors, which are: the length "d" of the propagation channel, i.e. the distance between the dipole emitter $D_e$ and the dipole receiver $D_r$; the orientation "α" of the dipoles $D_e$, $D_r$ with respect to each other; the inter-electrode distances "$d_{e1}$" and "$d_{e2}$" for the dipoles $D_e$, $D_r$, i.e. the distance between the electrodes E1, E2 and the distance between the electrodes E3, E4; and the electrical properties of the propagation medium.

As can be seen in FIG. 4, the electrodes E3, E4 form a dipole receiver the orientation of which differs from that of the dipole receiver formed by the electrodes E3, E4'. The difference in orientation between the dipoles E3, E4 and E3, E4' is illustrated by the angle α in FIG. 4.

When the implantable medical system according to the present invention is implanted in a human body, in particular in or in the vicinity of the heart, as shown by the system 10 in FIG. 1, by the system 11 in FIG. 2 and by the system 12 in FIG. 3, the electrical signal detected at the dipole receiver $D_r$ is modulated in amplitude. This results from the fact that respiration changes the properties of the environment, in particular the quantity of oxygen present in the lungs, which causes the attenuation of the electrical signal to vary during its transmission along the propagation channel, and thus causes a variation in the amplitude of the electrical signal which is detected then processed by means of an analysis module of the system according to the present invention.

In the following, the analysis module of the system of the present invention will be further described according to several embodiments.

Figure 5:
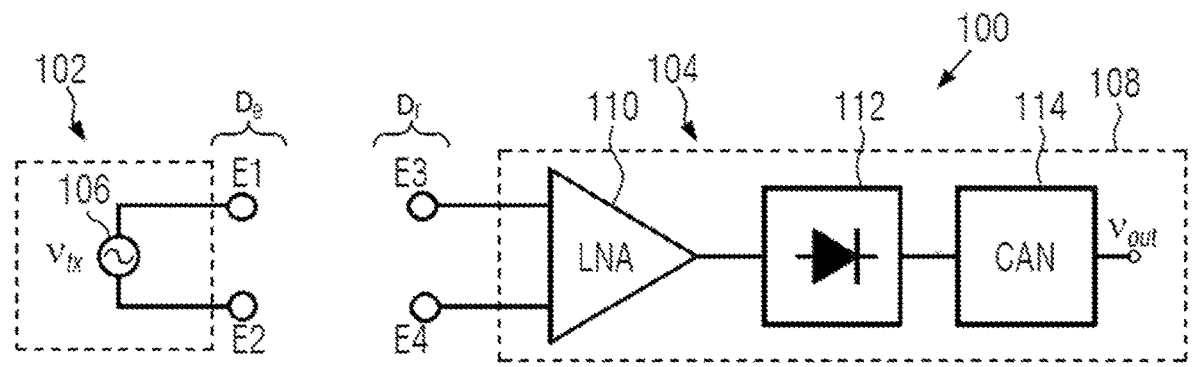
FIG. 5 shows a schematic view of a system according to the present invention comprising an analysis module according to a first embodiment.

FIG. 5 shows schematically a system 100 of the present invention comprising an analysis module according to a first embodiment.

The system 100 in accordance with the first embodiment of the invention comprises a first device 102 comprising a dipole emitter $D_e$ and a second device 104 comprising a dipole receiver $D_r$. The dipole emitter $D_e$ is formed by the pair of electrodes E1, E2 and the dipole receiver $D_r$ is formed by the pair of electrodes E3, E4. The dipole emitter $D_e$ is comprised in the implantable device 102 which is distinct from the device 104 comprising the dipole receiver $D_r$. Moreover, a pair of electrodes is arranged in a subcutaneous manner while the other pair of electrodes is formed by means of endocardial electrodes.

The dipole emitter $D_e$ is connected to a generator 106 at a defined frequency $f_0$, while the dipole receiver $D_r$ is connected to an analysis module 108. The generator 106 may be a voltage or current generator.

It should be noted that the frequency $f_0$ must be sufficiently high not to stimulate the heart of a patient by interfering with the normal cardiac activity of the patient.

Accordingly, the defined frequency $f_0$ is preferentially more than 1 kHz, in particular more than 10 kHz, so as not interfering with the physiological signals of the patient.

Advantageously, using a lower frequency, in particular below 10 kHz, allows saving energy.

The analysis module 108 comprises a front-end low noise amplifier 110 for amplifying the signal captured by the dipole receiver $D_r$ followed by an envelope detector 112. The amplifier 110 may comprise an analogue filter.

The envelope detector 112 performs an amplitude demodulation of the electrical signal by retrieving the information of the dipoles which may be correlated with hemodynamic parameters and respiratory frequency.

The envelope detector 112 is followed by an analogue-to-digital converter 114 configured to sample the captured electrical signal.

Figure 6:
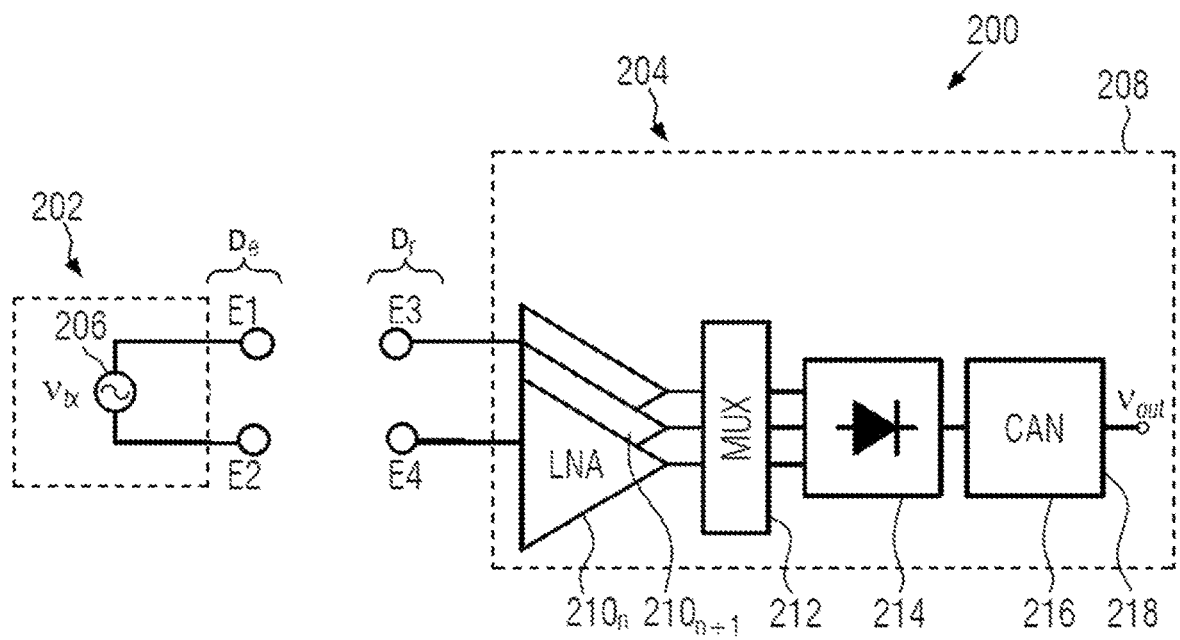
FIG. 6 shows a schematic view of a system according to the present invention comprising an analysis module according to a second embodiment.

FIG. 6 shows schematically a system 200 of the present invention comprising an analysis module according to a second embodiment.

The system 200 in accordance with the second embodiment of the invention comprises a first device 202 comprising a dipole emitter $D_e$ and a second device 204 comprising a dipole receiver $D_r$.

As in the first embodiment, the dipole emitter $D_e$ is formed by the pair of electrodes E1, E2 and the dipole receiver $D_r$ is formed by the pair of electrodes E3, E4. The dipole emitter $D_e$ is comprised in the implantable device 202 which is distinct from the device 204 comprising the dipole receiver $D_r$. Hence, the electrodes E1, E2 are distinct from the electrodes E3, E4. Moreover, a pair of electrodes is arranged in a subcutaneous manner while the other pair of electrodes is formed by means of endocardial electrodes.

The dipole emitter $D_e$ is connected to a generator 206 at a defined frequency $f_0$, while the dipole receiver $D_r$ is connected to an analysis module 108.

The dipole emitter $D_e$ of the system 200 may emit an electrical signal with variable amplitude. Thus, the amplitude of the electrical signal emitted by the dipole emitter $D_e$ can be adjusted once the implantable devices 202, 204, and thus the dipoles emitter/receiver, are implanted in a patient's body in order to obtain a suitable signal-to-noise ratio for detection at the dipole receiver $D_r$.

The implantable 204 may further comprise a telemetry module (not represented in FIG. 6) connected to the analysis module 208 and configured to communicate data to an external device (not represented in FIG. 6) so that, depending on the electrical signal captured, the amplitude of the electrical signal emitted by the dipole emitter $D_e$ can be adjusted by telemetry.

According to the second embodiment of the invention, the analysis module 208 comprises a plurality of n low noise amplifiers $210n$ selectable according to the position of the dipole emitter $D_e$ with respect to the dipole receiver $D_r$. In fact, the relative positioning of the dipole emitter $D_e$ in relation to each dipole receiver $D_r$ has an influence on the properties of the propagation channel of the electrical signal. Therefore, according to the channel attenuation caused by the mutual position of the implantable devices 202, 204, the implantable device 204 comprising the dipole receiver $D_r$ may select the low noise amplifier which gain is best adapted to the captured signal. In this manner, the energy consumption of the system 200 may be optimized by activating only the low noise amplifier necessary for providing sufficient detection of the electrical signal for the measurement, i.e. which satisfies a certain predefined signal-to-noise ratio.

In the analysis module 208 of the implantable device 204, the plurality of low noise selectable amplifier $210_n$ is followed by a multiplexer 212 itself followed by an envelope detector 214.

The analysis module 208 further comprises an analogue-to-digital converter 216 and digital filters 218 configured for processing the electrical signal captured by means of the dipole receiver $D_r$. Hence, after the envelope detector 214, the captured and detected signal may be sampled by the analogue-to-digital converter 216 of the analysis module 208 and digitally filtered for discriminating respiration information from hemodynamic information, as explained in the following.

The analysis module 208 comprises a digital filtering means. In particular, the analysis module 208 comprises a low pass digital filter configured to extract respiratory information from the captured electrical signal, more in particular a low pass digital filter with a cutoff frequency $f_c$ comprised between 0.5 Hz and 5 Hz, even more in particular with a cutoff frequency $f_c=1$ Hz.

The analysis module 208 further comprises a bandpass digital filter configured to retrieve hemodynamic information of the captured electrical signal, in particular a bandpass digital filter with a bandwidth comprised between 0.5 Hz and 30 Hz, more in particular between 1 Hz and 10 Hz.

The frequency range of 0.5 Hz to 30 Hz allows both filtering of the respiratory artifact by cutting frequencies below 0.5 Hz and filtering of high-frequency noises, i.e. noises with a frequency above 30 Hz, in particular the high-frequency noises with a frequency of the order of 50 to 60 Hz.

It should be noted that the frequency range selection for the bandpass digital filter may allow savings in terms of digital processing.

Hence, the system 200 may be used for retrieving hemodynamic information and respiration information from the same signal acquisition using digital filters 218 suitable to discriminate the different information.

Figure 7:
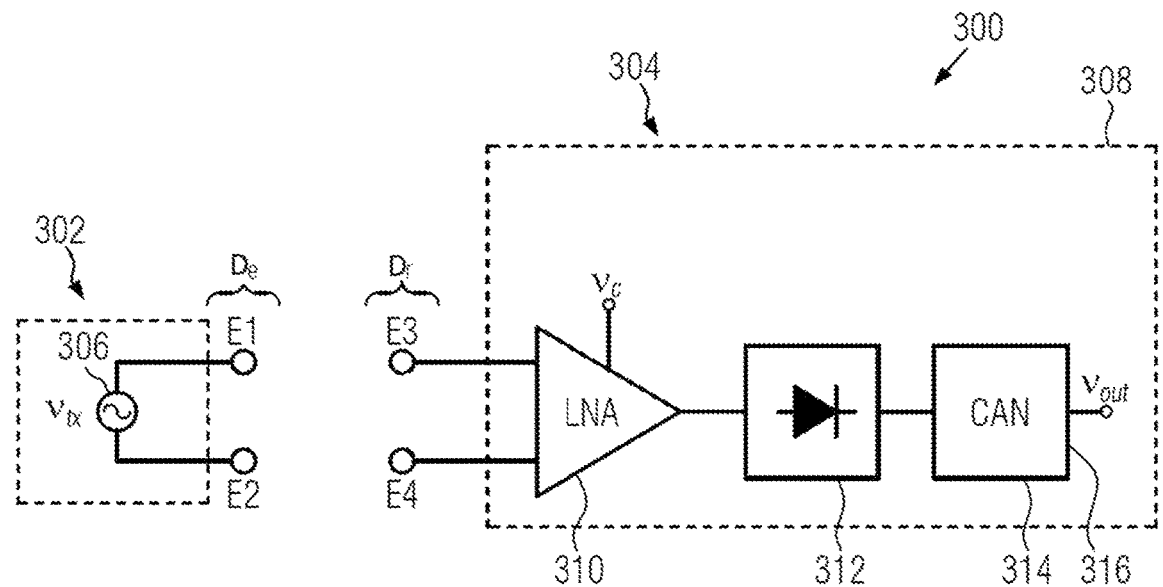
FIG. 7 shows a schematic view of a system according to the present invention comprising an analysis module according to a third embodiment.

FIG. 7 shows schematically a system 300 of the present invention comprising an analysis module according to a third embodiment.

The system 300 in accordance with the third embodiment of the invention comprises a first implantable device 302 comprising a dipole emitter $D_e$ and a second implantable device 304 comprising a dipole receiver $D_r$.

As in the first and the second embodiments, the dipole emitter $D_e$ is formed by the pair of electrodes E1, E2 and the dipole receiver $D_r$ is formed by the pair of electrodes E3, E4. The dipole emitter $D_e$ is comprised in the first implantable device 302 which is distinct from the device 304 comprising the dipole receiver $D_r$. Hence, the electrodes E1, E2 are distinct from the electrodes E3, E4. Moreover, a pair of electrodes is arranged in a subcutaneous manner while the other pair of electrodes is formed by means of endocardial electrodes.

The dipole emitter $D_e$ is connected to a generator 306 at a defined frequency $f_0$, while the dipole receiver $D_r$ is connected to an analysis module 308.

The analysis module 308 comprises variable gain amplifier 310 followed by an envelope detector 312. The variable gain amplifier 310 is controlled by adjusting a control voltage Vc.

In the same manner as the analysis module 208 described in reference of FIG. 6, the analysis module 308 comprises an analogue-to-digital converter 314 and digital filters 316. The analogue-to-digital converter 314 and the digital filters 316 are identical to those of the analysis module 208 in FIG. 6. Therefore, for the analogue-to-digital converter and the digital filters already used for the description in FIG. 6, reference is made to their descriptions above.

Figure 8:
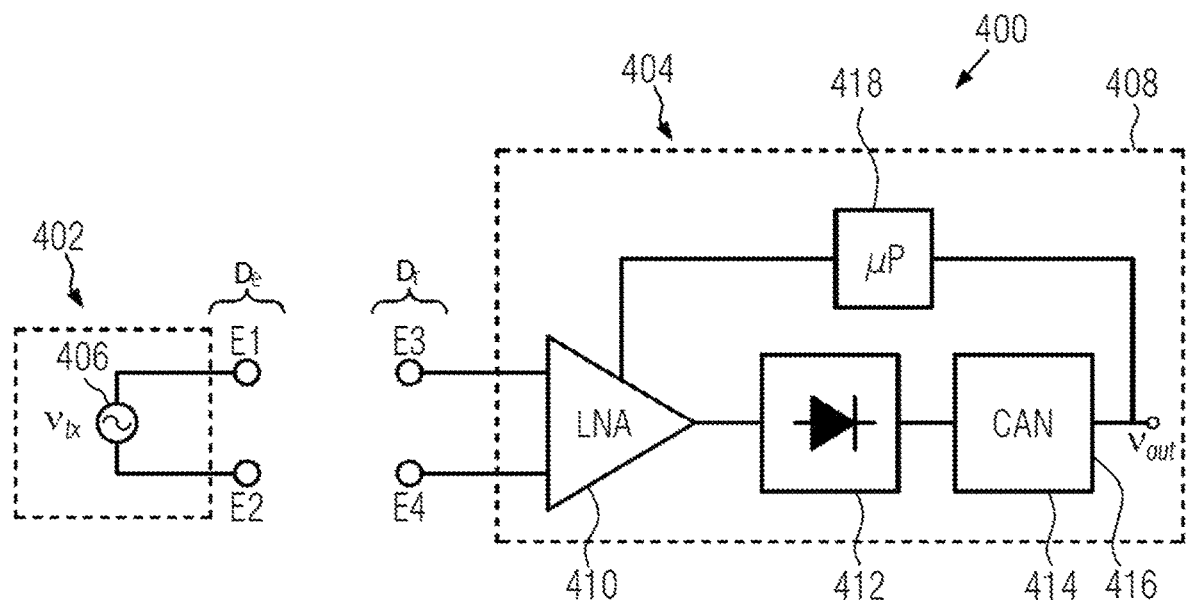
FIG. 8 shows a schematic view of a system according to the present invention comprising an analysis module according to a fourth embodiment.

FIG. 8 shows schematically a system 400 of the present invention comprising an analysis module according to a fourth embodiment.

The system 400 in accordance with the fourth embodiment of the invention comprises a first implantable device 402 comprising a dipole emitter $D_e$ and a second implantable device 404 comprising a dipole receiver $D_r$.

As in the preceding embodiments, the dipole emitter $D_e$ is formed by the pair of electrodes E1, E2 and the dipole receiver $D_r$ is formed by the pair of electrodes E3, E4. The dipole emitter $D_e$ is comprised in the first implantable device 402 which is distinct from the second implantable device 404 comprising the dipole receiver $D_r$. Hence, the electrodes E1, E2 are distinct from the electrodes E3, E4. Moreover, a pair of electrodes is arranged in a subcutaneous manner while the other pair of electrodes is formed by endocardial or epicardial electrodes.

The dipole emitter $D_e$ is connected to a generator 406 at a defined frequency $f_0$, while the dipole receiver $D_r$ is connected to an analysis module 408.

The analysis module 408 is comprised in the implantable second device 404 comprising the dipole receiver $D_r$.

The analysis module 408 comprises a programmable gain amplifier 410 followed by an envelope detector 412, an analogue-to-digital converter 414 and digital filters 416.

The analogue-to-digital converter 414 and the digital filters 416 are identical to those of the analysis module 308 in FIG. 7. Therefore, for the analogue-to-digital converter and the digital filters already used for the description in FIG. 7, reference is made to their descriptions above.

The programmable gain amplifier 410 is digitally controlled by means of an internal microcontroller 418.

Figure 9:
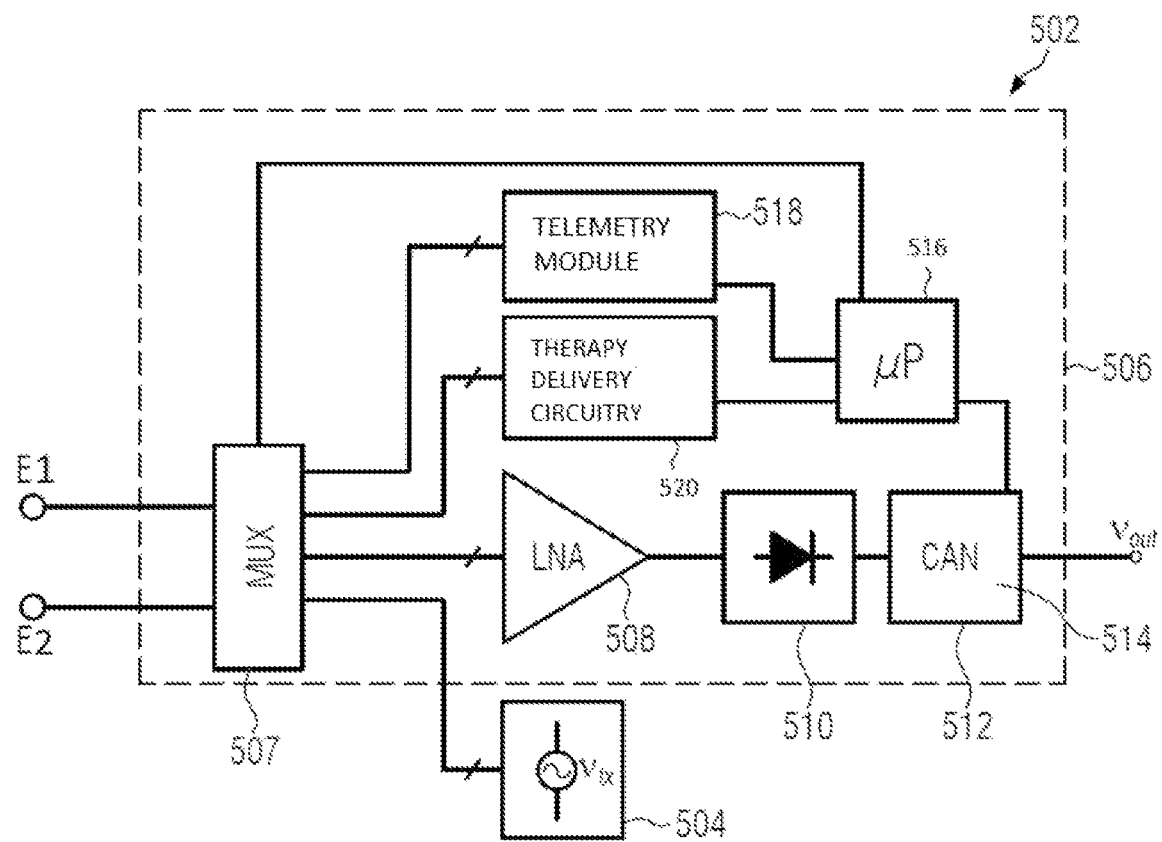
FIG. 9 shows a schematic view of an implantable device of a system according to the present invention.

FIG. 9 shows schematically an implantable device 502 comprised in a system according to the present invention.

The implantable device 502 is a subcutaneous implantable cardioverter defibrillator.

In a variation, the implantable device 502 is a subcutaneous loop recorder.

In a further variation, the implantable device 502 is an implantable endocardial device.

The implantable device 502 comprised two electrodes E1, E2 which may form a dipole receiver as well as a dipole emitter.

The implantable device 502 comprises a generator 504 which can be used as a generator for the dipole emitter E1, E2—in the case wherein the pair of electrodes E1, E2 forms a dipole emitter.

The implantable device 502 comprises an analysis and control module 506.

In the analysis and control module 506, after a multiplexer 507, the implantable device 502 comprises a low noise amplifier 508, an envelope detector 510, an analogue-to-digital converter 512 and digital filters 514.

As shown in FIG. 9, the analysis and control module 506 further comprises an internal microprocessor 516 connected to the analogue-to-digital converter 512 and to the digital filters 514 as well as to a telemetry module 518 and a therapeutic delivery circuit 520.

The system according to the present invention is thus configured for retrieving hemodynamic and respiration information from the same signal acquisition, in particular by means of digital filters 218 suitable to discriminate the different information.

It should be noted that in each of the electrodes dipole may act as the dipole emitter and also as the dipole receiver. The system according to the invention makes it possible to select the configuration of the dipoles which is the most sensitive and/or the most energy-saving.

The described embodiments are simply possible configurations and it should be borne in mind that the individual characteristics of the different embodiments can be combined with each other or provided independently of each other. Reference to the singular should also be interpreted as referring to the plural.

What is claimed is:

1. A system for measuring impedance, the system comprising:
    a first implantable medical device comprising at least one dipole emitter formed by two electrodes connected to a generator, the at least one dipole emitter configured to emit an electrical signal;
    a second implantable medical device distinct from the first implantable medical device and comprising at least one dipole receiver formed by two electrodes, the at least one dipole receiver of the second implantable medical device configured to capture the electrical signal emitted by the at least one dipole emitter of the first implantable medical device; and
    an analysis module comprising at least one amplifier and at least one envelope detector, the analysis module connected to the at least one dipole receiver, wherein the envelope detector is configured to demodulate the amplitude of the electrical signal captured by the second implantable medical device and the analysis module is configured to treat the demodulated electrical signal to determine a physiological parameter of a patient;
    wherein:
        one of the first implantable medical device or the second implantable medical device is a subcutaneous implantable cardioverter defibrillator or a subcutaneous loop recorder; and
        the other of the first implantable medical device or the second implantable medical device is an implantable endocardial device.

2. The system of claim 1, wherein the analysis module further comprises an analog-digital converter and at least one digital filter configured to treat the electrical signal captured by the second implantable medical device.

3. The system of claim 1, wherein the analysis module comprises a low pass digital filter configured to retrieve physiologic information from the electrical signal captured by the second implantable medical device.

4. The system of claim 3, wherein the low pass digital filter has a cutoff frequency between 0.5 Hz and 5 Hz.

5. The system of claim 1, wherein the analysis module comprises a bandpass digital filter configured to retrieve hemodynamic information of the electrical signal captured by the second implantable medical device.

6. The system of claim 5, wherein the bandpass digital filter has a bandwidth between 0.5 Hz and 30 Hz.

7. The system of claim 1, wherein the analysis module comprises a bandpass low noise amplifier configured to amplify the electrical signal captured by the at least one dipole receiver of the second implantable medical device.

8. The system of claim 1, wherein the analysis module comprises a plurality of low noise amplifiers, and wherein the plurality of low noise amplifiers are selectable based on a position of the at least one dipole emitter of the first implantable medical device with respect to at least one dipole receivers of the second implantable medical device.

9. The system of claim 1, wherein the implantable endocardial device is a leadless cardiac pacemaker.

10. The system of claim 9, further comprising a second leadless cardiac pacemaker, the second leadless cardiac pacemaker comprising at least one of a second dipole receiver or a second dipole emitter.

11. The system of claim 10, wherein an electrical pulse delivered by the at least one dipole emitter of the first implantable medical device or the second dipole emitter of the second leadless cardiac pacemaker is adapted based on a signal captured by the at least one dipole receiver of the second implantable medical device or the second dipole emitter of the second leadless cardiac pacemaker.

12. The system of claim 1, wherein the at least one dipole emitter emits an electrical pulse having a variable amplitude.

13. The system of claim 12, wherein the first implantable medical device further comprises a telemetry module configured to communicate with an external device, and wherein the variable amplitude of the electrical signal emitted by the at least one dipole emitter is adjustable based on a telemetry.

14. The system of claim 1, wherein the electrical signal is modulated via transmission through a propagation medium, and wherein the analysis module is further configured to demodulate the electrical signal to determine the physiological parameter of the patient.

* * * * *